(12) United States Patent
Delmotte (10) Patent No.: US 8,512,740 B2
(45) Date of Patent: Aug. 20, 2013

(54) FIBRIN FOAM AND PROCESS FOR MAKING

(75) Inventor: Yves A. Delmotte, Neufmaison (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 807 days.

(21) Appl. No.: 12/055,556

(22) Filed: Mar. 26, 2008

(65) Prior Publication Data

US 2009/0246261 A1 Oct. 1, 2009

(51) Int. Cl.
| | |
|---|---|
| *A61F 13/00* | (2006.01) |
| *A61L 15/16* | (2006.01) |
| *A61L 15/00* | (2006.01) |
| *A61K 9/70* | (2006.01) |
| *A61K 38/36* | (2006.01) |
| *A61K 35/14* | (2006.01) |
| *A61P 7/04* | (2006.01) |
| *A61P 7/02* | (2006.01) |
| *C07K 14/74* | (2006.01) |
| *C07K 14/475* | (2006.01) |
| *C07K 14/745* | (2006.01) |

(52) U.S. Cl.
USPC ........... 424/443; 424/444; 424/445; 424/446; 424/447; 514/13.6; 514/13.7; 530/382

(58) Field of Classification Search
None
See application file for complete search history.

(56) References Cited

U.S. PATENT DOCUMENTS

| | | | |
|---|---|---|---|
| 2,492,458 A * | 12/1949 | Bering, Jr. | 424/443 |
| 3,861,652 A | 1/1975 | Clark et al. | |
| 4,631,055 A | 12/1986 | Redl et al. | |
| 4,846,405 A | 7/1989 | Zimmermann | |
| 4,978,336 A | 12/1990 | Capozzi et al. | |
| 5,116,315 A | 5/1992 | Capozzi et al. | |
| 5,318,524 A * | 6/1994 | Morse et al. | 604/82 |
| 5,368,563 A | 11/1994 | Lonneman et al. | |
| 5,443,183 A | 8/1995 | Jacobsen et al. | |
| 5,474,540 A | 12/1995 | Miller et al. | |
| 5,582,596 A | 12/1996 | Fukunaga et al. | |
| 5,605,255 A | 2/1997 | Reidel et al. | |

(Continued)

FOREIGN PATENT DOCUMENTS

| | | |
|---|---|---|
| DE | 203 07 153 U1 | 9/2003 |
| WO | 96/39212 | 12/1996 |

(Continued)

OTHER PUBLICATIONS

Fritz. Business Briefing: Medical Device Manufacturing & Technology, 2002.*

(Continued)

*Primary Examiner* — Isis Ghali
(74) *Attorney, Agent, or Firm* — K&L Gates LLP (57) ABSTRACT

A fibrin wound dressing is made by mixing quantities of fibrinogen solution and thrombin solution with air. The resulting foam is very light weight, and with the proper attention to the amount of thrombin, will rest on a vertical surface without dripping. The wound dressing may also be formulated for its ability to continue migration of healing substances, such as PDGF, from the dressing to the wound site. Thrombin substitutes, such as other clotting proteins, may be used instead of thrombin. The resulting foam may also be lyophilized or ground and lyophilized for later reconstitution. A therapeutic drug or other additive may also be added to the wound dressing. A fibrin foam may be made by injecting fibrinogen foam into a clotting protein, such as thrombin.

31 Claims, 3 Drawing Sheets

(56) References Cited

U.S. PATENT DOCUMENTS

| | | | |
|---|---|---|---|
| 5,665,067 A | | 9/1997 | Linder et al. |
| 5,989,215 A | | 11/1999 | Delmotte et al. |
| 6,132,396 A | | 10/2000 | Antanavich et al. |
| 6,328,229 B1 | | 12/2001 | Duronio et al. |
| 6,383,422 B1 | * | 5/2002 | Hoffschmidt ............... 264/44 |
| 6,454,739 B1 | | 9/2002 | Chang |
| 6,461,361 B1 | | 10/2002 | Epstein |
| 6,548,729 B1 | | 4/2003 | Seelich et al. |
| 6,585,696 B2 | | 7/2003 | Petersen et al. |
| 6,620,125 B1 | | 9/2003 | Redl |
| 6,802,822 B1 | | 10/2004 | Dodge |
| 6,808,691 B1 | * | 10/2004 | Herve et al. ............... 422/294 |
| 6,884,232 B1 | | 4/2005 | Hagmann et al. |
| 6,921,381 B2 | | 7/2005 | Spero et al. |
| 7,135,027 B2 | * | 11/2006 | Delmotte ............... 606/93 |
| 2003/0146113 A1 | | 8/2003 | Unkrig et al. |
| 2006/0009801 A1 | | 1/2006 | McGurk et al. |
| 2006/0211802 A1 | * | 9/2006 | Asgari ............... 524/439 |

FOREIGN PATENT DOCUMENTS

| | | | |
|---|---|---|---|
| WO | WO 96/39212 | * | 12/1996 |
| WO | 2004/024306 A1 | | 3/2004 |
| WO | 2005/048977 A | | 6/2005 |
| WO | 2007/084919 | | 7/2007 |
| WO | 2007/084919 A1 | | 7/2007 |
| WO | 2009/083544 | | 7/2009 |

OTHER PUBLICATIONS

Porex Porous Products Group, "Products & Services", catalog, www.porex.com, Fairburn, GA.
Porex Porous Products Group, "Mupor(tm) Membrane Applications Brief", catalog, www.porex.com, Fairburn, GA.
Porex Porous Products Group, "Interact W/Innovation . . . discover the advantages of Porex", catalog, www.porex.com, Fairburn, GA.
Porvair Filtration Group, "Sintered Porous Materials", catalog, www.porvairfiltration.com, Fareham, Hampshire UK.
Merck Index, "No. 7498", 9th edition, p. 996.
International Search Report and Written Opinion for International Application No. PCT/US2009/034846 dated May 26, 2010.
European Office Action issued on Jul. 2, 2012 for corresponding European Appln. No. 09 725 797.6-1219.
Notification of Transmittal of the International Preliminary Report on Patentability for International Application No. PCT/US2009/034846 dated Oct. 8, 2010.
Porvair Filtration Group Ltd, "Developments in porous polymeric materials", Press Release, Sep. 2005, Fareham, Hampshire UK.
U.S. Appl. No. 11/624,113, filed Jan. 17, 2007.
Porex Porous Products Group, "Mupor(tm) Membrane Applications Brief", catalog, www.porex.com, Fairburn, GA, 2001.
Porvair Filtration Group, "Sintered Porous Materials", catalog, www.porvairfiltration.com, Fareham, Hampshire UK, Sep. 2005.
Shanbrom, E. et al., "Total Fibrin 'Super Glue' Components From Human Plasma: A New Blood Banking Procedure", Journal of Thrombosis and Haemostasis, Aug. 1, 2007, vol. 5, Supplement 1, Acta Physiologica Congress, Oxford, UK.
Andras Gruber et al., "Alteration of Fibrin Network by Activated Protein C", Blood, May 1, 1994, pp. 2541-2548, vol. 83, No. 9.
Matras, Helene, "Fibrin Seal: The State of the Art", J Oral Maxillofac Surg, 1985, vol. 43, pp. 605-611, W. B. Saunders Co., Philadelphia, PA.
Gibble J.W. et al., "Fibrin glue: the perfect operative sealant?", Transfusion, 1990, vol. 30, No. 8, pp. 741 to 747, Baltimore MD.

* cited by examiner

FIBRIN FOAM AND PROCESS FOR MAKING

BACKGROUND

The invention is in the field of medical science and surgery, and in particular in the field of wound dressings. Foaming of combined fluid streams, including fluid streams of different viscosities, may be useful in a wide variety of settings including the medical field, the food industry, electronics, automotive, cosmetic, energy, petroleum, pharmaceutical, chemical industries, manufacturing and others. In the fuel or energy industries, inline mixing of air, water or other components with fuel may be helpful to increase engine yield, create environmentally safer or cleaner fuels.

It has been known for some time that mixtures of fibrinogen and thrombin may be applied to wounds, such as open wounds of a person, to close the wound, stop the bleeding, and prevent other substances, such as infectious agents, from entering the wound. Fibrin is a well known tissue sealant that is made from a combination of at least two primary components, fibrinogen and thrombin, which have viscosities that depend greatly on the temperature. For example, the viscosity of fibrinogen varies from about 350 cst at 15° C. to less than 100 cst at 37° C. Upon coming into contact with each other, the fibrinogen and thrombin interact to form a tissue sealant, fibrin. The quality of the fibrin generated will substantially depend on the completeness of the mixing of the two components.

Fibrinogen and thrombin are generally provided in lyophilized form and stored at very low temperatures. Lyophilized fibrinogen is typically reconstituted with sterile water before use. Thrombin is also reconstituted with sterile calcium chloride or water, such as distilled water, before use. Saline, phosphate buffered solution (PBS), or other reconstituting liquid can also be used. In preparing fibrin, the reconstituted fibrinogen and thrombin are then combined to form fibrin.

In-line mixing techniques have been discovered for mixing thrombin and fibrinogen to form a wound sealant. The sealant may be applied by a dispenser that ejects the sealant directly onto the tissue or other substrate or working surface. Examples of tissue sealant dispensers are shown in U.S. Pat. Nos. 4,631,055, 4,846,405, 5,116,315, 5,582,596, 5,665,067, 5,989,215, 6,461,361 and 6,585,696, 6,620,125 and 6,802,822 and PCT Publication No. WO 96/39212, all of which are incorporated herein by reference. Further examples of such dispensers also are sold under the Tissomat® and Duploject® trademarks, which are marketed by Baxter AG.

Typically, in these prior art devices, two individual streams of the fibrinogen and thrombin components are combined and the combined stream is dispensed to the work surface. Combining the streams of fibrinogen and thrombin initiates the reaction that results in the formation of the fibrin sealant. The liquid fibrin sealant is frequently referred to as a fibrin gel. While thorough mixing is important to fibrin formation, fouling or clogging of the dispenser tip can interfere with proper dispensing of fibrin. Clogging or fouling may result from contact or mixing of the sealant components in the dispenser and the formation of a significant quantity of viscous fibrin in the passageway prior to ejection of the components from the dispensing tip.

This clogging may be found to be more prevalent when using a high concentration of thrombin, such as 250 IU/ml. High concentrations of thrombin also result in a much faster setting time, which is desired in certain applications, but may also result in incomplete mixing and binding between the thrombin and the fibrinogen, and thus an incomplete formation and release of fibrin to enable clotting. If the formulation also includes growth factor, such as platelet development growth factor (PDGF), it is believed that a high thrombin concentration causes poor binding of the growth factor to fibrin and therefore a poor release into the wound, where it would otherwise help to control clotting and tissue healing over time. Failure to clot as a result of the fibrin sealant curing too quickly may lead to further bleeding, causing additional loss of blood from the wound, and at a minimum delaying healing of the wound and possibly requiring further attention from a medical professional.

Curing too quickly thus may increase the tendency to clog the dispensing tip, impede clotting and delay healing of the wound. However, the curing may also occur too slowly, such as when low concentrations of thrombin are used. If the sealing compound does not cure and become firm reasonably quickly, the sealing compound may fall away or drip from the wound. If blood or other body fluids are involved, this may lead to a greater tendency to drip away from the wound and may also create a very unsightly and potentially hazardous condition. If the compound has fallen away from the wound site, and is not present, it cannot help to seal the wound or release fibrin into the wound to encourage clotting.

One innovation to solve these problems has been to mix air with fibrinogen and thrombin, as seen in U.S. patent application Ser. No. 11/624,113, filed Jan. 17, 2007, which is assigned to the assignee of the present patent, and which is hereby incorporated by reference. This patent application proposes mixing 1 ml aqueous fibrinogen at about 100 mg/ml concentration in one container, with another container having 1 ml thrombin at about a 4 IU/ml concentration and 2.5 ml air. The mixing technique includes transferring the components back and forth several times, at least two times, to create a fibrin foam. This foam has a relatively higher volume of air and, of course, a low density, a low concentration of fibrinogen and thrombin per unit volume, and a resulting low concentration of fibrin per unit volume in the foam. This low concentration results in a very long setting time to create a fibrin network. The drawback is that the conventional procedure to make a fibrin glue remains a technique based on use of equal volumes of fibrinogen and thrombin. The main feature of the foam is its low density, and therefore it is important to reduce the volume of diluent used or to increase the percentage of air in the foam formulation, or both.

What is needed is a better way to formulate wound dressings that will yield a firm, adherent wound dressing while controlling clotting and tissue healing.

SUMMARY

One embodiment is a method of forming a fibrin foam. The method includes steps of preparing a fibrinogen foam by mixing air with a solution of fibrinogen, and injecting the fibrinogen foam into a solution of thrombin to form a fibrin foam. Another embodiment is a method of forming a fibrin foam. The method include steps of preparing a fibrinogen foam by mixing air with a solution of fibrinogen in a hand-held mixing device, and injecting the fibrinogen foam into a solution of thrombin to form a fibrin foam. Another embodiment is a method for forming a fibrin foam. The method includes steps of preparing a fibrinogen foam by mixing a fibrinogen solution and air, and injecting the foam into a solution of a clotting protein to form a fibrin foam.

Another embodiment is a wound dressing made of a made of a fibrin foam. The wound dressing includes a quantity of fibrinogen, a quantity of a clotting protein, and a quantity of air mixed with the fibrinogen and the thrombin, wherein the quantity of fibrinogen includes a water solution with a concentration of fibrinogen and the quantity of clotting protein includes a water solution of clotting protein with a concentration of a clotting protein, and wherein the wound dressing is made by mixing the quantity of fibrinogen with the quantity of air to form a foam, the foam then mixed with the solution of clotting protein to form a wound dressing, and wherein the wound dressing is sufficiently firm to adhere to a vertical surface.

Another embodiment is a wound dressing kit. The wound dressing kit is made of a quantity of aqueous fibrinogen in a first container, a quantity of aqueous thrombin in a second container, and a quantity of gas, wherein the quantity of aqueous fibrinogen is configured for mixing with the quantity of gas in a first mixing container capable of being held in a hand of a user to form a fibrinogen foam, and the quantity of aqueous thrombin is configured for receiving the fibrinogen foam in a second mixing container capable of being held in a hand of a user to form a foamed wound dressing, and further comprising the first and second mixing containers capable of being held in a hand of a user.

Additional features and advantages are described herein, and will be apparent from, the following Detailed Description and the figures.

DETAILED DESCRIPTION

Fibrinogen is cleaved and polymerized into fibrin using thrombin in a well-characterized process. Thrombin, a protease or enzyme, cleaves fibrinogen, forming fibrin monomers. Once the fibrinogen is cleaved, a self-assembling step occurs in which the fibrin monomers come together and form a covalently crosslinked fibrin network in the presence of Factor XIII, normally present in blood. In the presence of calcium, thrombin transforms Factor XIII into Factor XIIIa, forming a proteinaceous network. This helps to close the wound and promote healing of the site. The fibrin network forms an excellent wound dressing which is applied to a wound site on a patient, such as a surgical field. Using the techniques described herein, thrombin concentrations from 5 to 20 IU/ml may be used even if both components are used at reduced temperature, such as 15° C. Thrombin concentration may be as high as 500 IU/ml and the concentration of fibrinogen can be as low as 3 mg/ml.

In work done to date, temperature has had little effect on mixing. Foams have been made from fibrinogen and thrombin as described below at 4° C., 18°, 27° and 37°. Because of this remarkable ability, the fibrinogen and thrombin do not need to be pre-warmed before they are mixed in operating rooms, which are normally between about 18 to 22° C. This may be because of the inherent low thermal capacity of foams, as compared to full-density liquids or mixtures.

The components may be kept in sterile packages, double blister packs. Operating room personnel need only unpack the outer blister pack and transfer the inner blister pack, sterile inside and out, to the sterile nurse. The fibrinogen solution is held in a first container, which may be a sterile hand-held mixer as disclosed herein, or may be a different container. The solution of thrombin or other clotting protein is held in a second container, which may be a portion of the sterile hand-held mixer as disclosed herein, or may be another container. The sterile nurse then prepares the fibrin foam for the surgeon. This eliminates the need for a circulating nurse to warm and reconstitute the foam, since the sterile nurse can easily and quickly mix the foam, no pre-warming needed, with embodiments as described herein.

It has also been discovered that a fibrin foam may be reliably formed by initially foaming the individual component, fibrinogen. In one example of how to form a fibrinogen foam, the fibrinogen foam is formed or generated using the mixer of FIG. 1.

Several experiments were conducted using this technique. The fibrinogen foam was made using the mixing technique described here, one syringe including 0.5 ml fibrinogen and the other including 1.0 ml air. The two were mixed about 4 to about 10 times by alternately pushing on one plunger and then the other.

Figure 1:
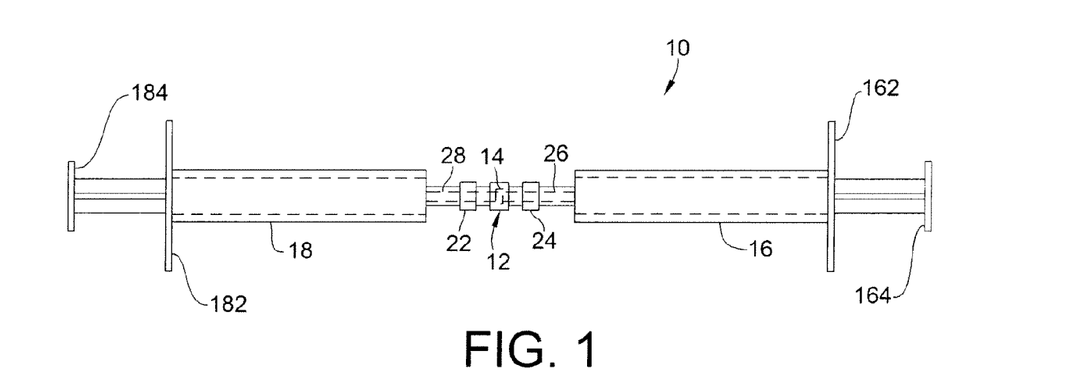
FIG. 1 is a first embodiment of a hand-held mixing device for generating fibrinogen foam.

As seen in FIG. 1, a foam-producing device 10 includes a mixer holder 12 with a mixing device or mixer 14 between two containers 16, 18 (e.g., syringes) each holding a fluid (liquid or gas). Each syringe 16, 18, has a plunger 164, 184, and a finger grip or finger rest 162, 182. The portions of the combined device that hold mixer holder 12 can be integrated with the dispensers or may be connectors. The connectors 22, 24 are each connected to one of the dispensers 16, 18. Materials for syringes may include polyethylene, polypropylene, cyclic olefin copolymers (COC), and other suitable materials. The plungers or pistons, or at least their tips, may be made from an elastomer, such as silicone. Alternatively, silicone may be eliminated in the plungers if they are made from a less expensive material, such as thermoplastic elastomer, and then coated with a fluorinated coating, such as Fluorotec®, or others available from Dalkyo Seiko, Ltd., of Tokyo, Japan.

By way of example and not limitation, embodiments provide a method for mixing at least two foam components, where each component is separately located in one of the containers 16, 18. Each container includes a distal passageway 26, 28, respectively, with which each fluidly communicates with the mixer 14 and the other syringe or container. The distal passageways of the syringes may be two female luer connectors and the mixer holder 12 may includes two male luers on its ends or other desired combination thereof, as desired.

When it is desired to mix the components, one component, such as fibrinogen, which, for example is located in the left dispenser 18 is urged from one (or first) side of the device to another (or second) side of the mixer by depressing plunger 184 and holding the syringe by finger grip 182, thereby allowing flow into the other container 16 on the right side, where, for example, air is located. The two components are allowed to flow from the container 18 through the inline mixer 14 to the other container 16, thus mixing the fibrinogen and air to form a fibrinogen foam. The process may then be repeated, and the foam pushed from container 16 to container 18 by depressing plunger 164 while holding finger grip 162. Each time the foam passes through the mixer 14, further mixing between the components is provided. It is contemplated that the components may pass through the mixer 14 at least once, but additional passes through the mixer will achieve thorough mixing. The number of transfers during the formation of the fibrinogen foam, and the characteristics of the porous material used, will determine the bubble size of the fibrin foam, which can range, in these experiments, from about 300 μm initially, down to about 10 μm when about 8 transfers are made with a Vyon F mixer. In another technique, fibrinogen solution and air may be placed in one container and then transferred or swooshed into the other, and then back and forth several times, to form the fibrinogen foam.

Bottom-Up Fibrin Foam Formation

Figure 2:
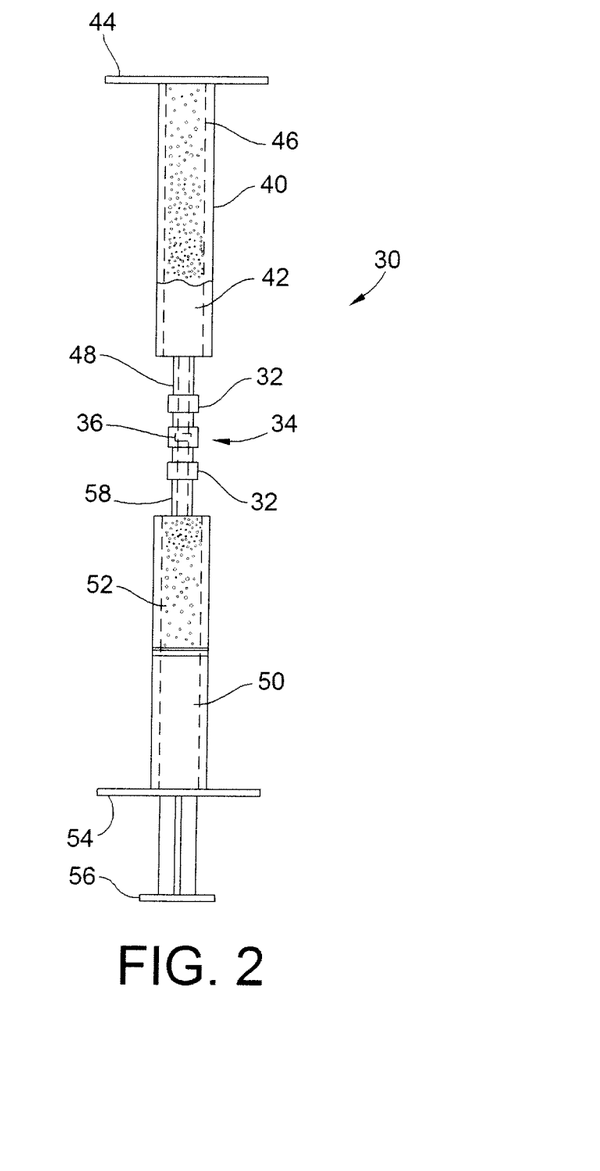
FIG. 2 depicts a second use of a hand-held mixing device to generate fibrin foam by injection of fibrinogen foam through a thrombin solution.

In an application, a syringe of fibrinogen foam is prepared from a mixture of aqueous fibrinogen and air, using syringes such as those depicted in FIG. 2. The assembly 30 of FIG. 2 depicts a lower syringe 50 which has been used in the process described above to form a fibrinogen foam 52. Lower syringe 50 also includes a finger rest 54 and plunger 56. The fibrinogen foam is generated as discussed above for FIG. 1 and the connectors removed. Syringe 50 with foam 52 is then connected to the upper syringe 40, upper syringe 40 including a finger rest 44 and holding a thrombin solution 42. The syringes are then connected via their distal portions 48, 58, with connectors 32, such as luer connectors, and an inline mixing device 36 within housing 34. The two are inverted, as shown in FIG. 2, syringe 40 with the thrombin solution 42 on top and syringe 50 with the foamed fibrinogen on the bottom.

The foamed fibrinogen is then injected into upper syringe 40 with the thrombin 42, and a fibrin foam 46 is formed very quickly as the stream of fibrinogen foam makes its way to the top of the upper syringe and the thrombin solution. The fibrinogen foam will mix with an amount of the thrombin and the foam will move to the top of the upper syringe because the foam is much lighter than the liquid thrombin into which it is injected. Upon contact between the thrombin solution and the fibrinogen foam, the fibrin foam begins forming. The fibrin foam that is formed is also much lighter than the liquid thrombin and will thus move to the top. The excess liquid thrombin remains at the bottom and is discernible, as it is still clear. The excess may then be removed by inserting and actuating a plunger on the upper syringe (not shown) to inject into lower syringe 50 which previously housed the fibrinogen foam. This leaves the fibrin foam in the upper syringe. The excess thrombin can also be removed by pulling plunger 56 down in order to aspirate the excess thrombin into syringe 50.

This process allows the use of the components in ratios other than 1:1. The foam may thus use less liquid and may be made lighter. For example, in one experiment, 2 ml of aqueous fibrinogen at a concentration of 100 mg/ml is mixed with 2 ml air to form about 4 ml fibrinogen foam. The syringe with the foam is placed underneath, bottom-up, a syringe containing 3 ml aqueous thrombin at 4 IU/ml. The fibrinogen foam is then urged into the aqueous thrombin, forming fibrin foam. When the excess liquid thrombin solution was removed from the upper syringe, it was found that only 0.4 ml of thrombin solution had been used. This method thus uses small amounts of thrombin and still achieves a foam useful for wound dressings. The fibrin foam is sufficiently viscous that it can then be directly applied to the wound, using only the luer tip of the upper syringe. Alternatively, a cannula or needle may be connected to the luer tip for application to the wound. Depending on the desired form of the mixture to be applied, and the work surface used, other types of dispensing devices may also be used, such as a catheter or a spray head.

Alternatively, the fibrin foam may be used to fill a device such as a spinal fusion cage in an operating room or in a manufacturing plant to fill molds for lyophilization, the material then suitably packed and stored for shipment to customers, as described in the example below.

Very Firm Foams

If very firm foam is desired, aqueous thrombin at a much higher concentration, such as 250 to 500 IU/ml may be used in the upper container, as depicted in FIG. 2. Fibrinogen solutions with concentrations from about 1 mg/ml to about 100 mg/ml may be used. This may result in a fibrin foam that takes the shape of the upper syringe or other container used to hold the aqueous thrombin or other clotting protein. The formation occurs so quickly that the foam cannot be applied from the syringe or container if the proportions of thrombin or clotting protein and fibrinogen foam are sufficiently high. The fibrin foam will then take on the shape of the container and upon removal will retain this shape. This allows the user to select the shape of the resulting product. Thus, if a different shape is desired, the fibrinogen foam may be injected into a container of the desired shape, the container holding a solution of thrombin or other clotting protein, in which the thrombin or other clotting protein is present at a high concentration. As described below, foams with these shapes may also be freeze dried (lyophilized) and stored for later use, or may be freeze dried and ground into a powder for later reconstitution and use.

Manipulable or Formable Foams

Figure 3:
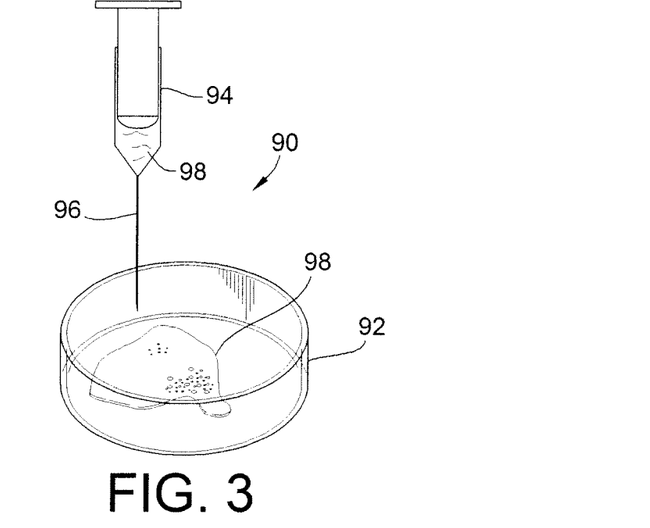
FIG. 3 depicts manipulation of fibrin foam after foam formation.
Figure 4:
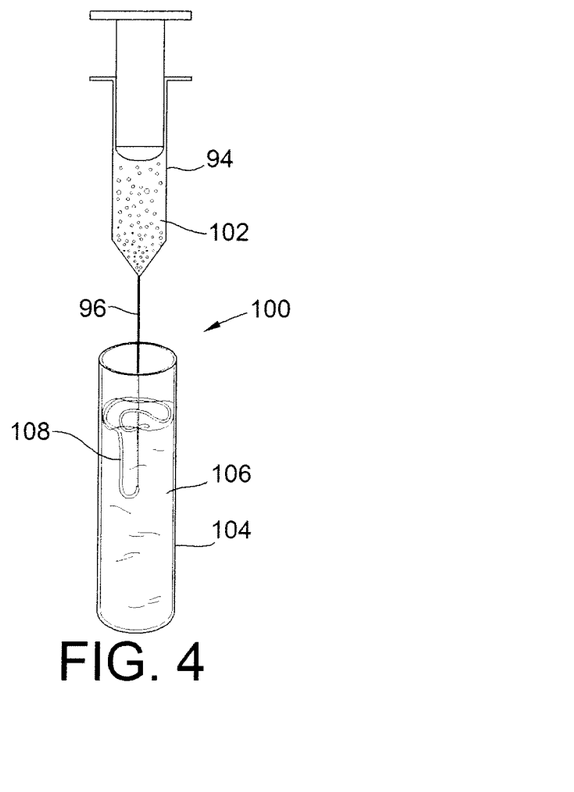
FIG. 4 depicts injection of fibrinogen solution into a thrombin solution to form fibrin foam.

Other techniques may also be used to manipulate and shape the foam, as depicted in FIGS. 3 and 4. In FIG. 3, equipment 90 for one technique is disclosed. A watch glass 92 receives foamed fibrin 98 from syringe 94, the fibrin formed from foamed fibrinogen and liquid thrombin, using dispenser needle 96 to inject the foamed fibrin. Once the foam is placed into the watch glass, is may be manipulated into a desired shape for an application. FIG. 4 discloses different equipment for another technique. Fibrinogen foam 102 is injected from a syringe 94 and needle or cannula 96 into a solution 106 of thrombin or other clotting protein, in this example near the bottom of a vial 104. This technique results in a fibrin foam 108. The fibrin foam 108 is formed in the shape of a continuous, thick cylinder, and since it has a lower density, it will also rise to the top of vial 104. The size of the foam cylinder formed depends on the gage of the needle. Beads of foam may also be formed by co-injecting fibrin foam and air alternately into the thrombin solution. The concentration of thrombin solution used in this technique is lower, for example from about 4 IU/ml to about 20 IU/ml. Other concentrations may be used, for example from about 0.1 IU/ml to about 500 IU/ml. Fibrinogen solutions with concentrations from about 1 mg/ml to about 100 mg IU/ml may be used.

If it is desired to make a patch of another desired shape, for instance, a round patch, the technique of FIG. 3 above may be used and the fibrin foam manipulated in the bottom of the watch glass to the desired shape. The patch will have the round shape of the bottom of the watch glass and the thickness will be that allowed by the quantity of fibrin foam. This may be useful if quantities of fibrin foam are produced for lyophilization and later reconstitution in that shape as a wound dressing, without the need for extensive laboratory equipment or facilities. For example, useful shapes for later processing include spheres cylinders, and flat surfaces of different thicknesses. These may be made using fibrinogen foam at a suitable concentration and thrombin solution to form fibrin foam in any desired shape. The concentrations of the fibrinogen and thrombin used are determined based on the requirements of the fibrin foam, such as clotting time needed, mechanical strength properties, any needed elongation or stiffness, and so forth.

Inline Mixer materials

The inline mixer is made from a polymeric material formed by sintering to define an integral porous structure. The lattice or matrix of polymeric material forms a plurality of essentially randomly-shaped, tortuous interconnected passageways through the mixer. The material of the inline mixer 36 may be selected, for example, from one or more of the following: polyethylene (PE), high density polyethylene (HDPE), polypropylene (PP), ultra high molecular weight polyethylene (UHMWPE), nylon, polytetrafluorethylene (PTFE), polyvinylidenefluoride (PVDF), polyester, cyclic olefin copolymer (COC), thermoplastic elastomers (TPE) including EVA, polyetheretherketone (PEEK), glass, ceramic, metal, other polymer materials, or other similar materials. Inline mixers may also be made of a polymer material that contains an active powdered material such as carbon granules or calcium phosphate granules with absorbed molecules. Other types of materials are also possible. A sintered polypropylene material suitable for the present embodiments may be available from commercial sources, such as from Bio-Rad Laboratories, Richmond, Calif., United States, Porex Porous Products Group of Porex Manufacturing, Fairburn, Ga., United States, Porvair Technology, a Division of Porvair Filtration Group Ltd., of Wrexham, United Kingdom, including Porvair Vyon Porvent, PPF or PPHP materials, or MicroPore Plastics, Inc., of 5357 Royal Woods, Parkway, Tucker, Ga., U.S.A.

It is also possible that the inline mixer may be made of one or more materials having one or more characteristics that may assist mixing of the component streams. By way of example and not limitation, the material may be hydrophilic, which is material that absorbs or binds with water, or hydrophobic, a material which is essentially repels and does not bind with water. The material may also be oleophobic, i.e., resistant to absorption of oils and the like, and may have other desirable characteristics that enhance mixing of the components.

Additional Foam Components

One or more additional component or agent may be premixed with one or more of the components, such as the fibrinogen or thrombin, or both in the respective component container. Alternatively, an additional component or components may be stored in a separate container as a liquid or in a lyophilized form for mixing with one or more components during use of the foam mixer, the foam dispenser, or both the foam mixer and dispenser. The additional component or components may be stored in the same container as frozen separated liquids, the separation performed by a layer of frozen water. They may also be stored as separated layers of lyophilized fibrinogen and thrombin separated from each other because the water frozen layer separating the two active ingredient has been sublimed during freeze drying. In another method, they may be stored as a mixture of lyophilized fibrinogen and thrombin. In this case, when making fibrinogen foam, one syringe contains the component and a second syringe contains air and a diluent, and may also contain any of the active components described above or below.

As an example, and with respect to FIG. 1, a desired amount of a lyophilisate of fibrinogen is placed into syringe 18. An appropriate mixture of sterile water and air (diluent) is placed into syringe 16. Plunger 164 is then depressed to transfer the diluent into syringe 18. After allowing a certain amount of time for reconstitution, and when the fibrinogen is completely dissolved, plunger 184 is actuated, pushing the fibrinogen foam into syringe 16, and several more transfers are accomplished for thorough mixing to form a satisfactory fibrinogen foam. This process may also be used with one or more additives.

For a dispenser or mixer, such as in any of the above described embodiments, in which one or more of agents are employed, the combined stream provides a sufficiently thoroughly mixed sealant or wound dressing, such as fibrin wound dressing, in which the antibiotic, drug, hormone, or other agent or agents are well dispersed throughout the sealant. Such antibiotic, drug, hormone, or other agent may allow controlled release over time to the applied working surface, for example, to aid in post-operative or surgical treatment. It is contemplated that various agents may be employed depending on the desired application and the combined fluid stream.

These components include Factor XIII, a calcium compound, human or animal or vegetal protein solutions containing collagen, oxidized collagen, growth factors, coagulation factors, fibronectin, plasminogen or plasminogen inhibitor or both plasminogen and plasminogen inhibitor. A plasminogen inhibitor is one which inhibits the conversion of plasminogen in plasmin, such as aprotinin, tranexanic acid, a2-antiplasmins, a2-macroglobulins, a2-antitrypsin, antithrombin, anti-streptokinase, aminocapronic acid, tranexamic acid, Cl-esterase inhibitor, anti-urokinase, and the like. Components for activating the conversion of plasminogen into plasmin may also be used, such as t-PA, u-PA, streptokinase, altephase, and the like, and albumin, casein, soya, and amino acids. These may be used in combination with mono-, di-, tri, and polysaccharides or mucoopolysaccharides. These may include carrageenan, agarose, cellulose, methylcarboxycellulose, chitin, chitosan, alginic acid, glycosaminoglycans, hyaluronic acid and chondroitin sulfate, or the derivatives thereof.

They may also be used with polyglycols or other glycols and high molecular weight alcohols, such as glycerol, ethylene glycol, 1,3-propanediol, propylene glycol, sorbitol, sorbitan, mannitol, diglycerol, butanediol, and urea, or mixtures thereof. Glycerol and propylene glycol are useful plasticizers, as are the esters of polyols, such as glycerol monoacetate and glycerol diacetate. Also useful are hydrophilic polymers that have a molecular weight of 1,000 Da to 15,000 Da, also between 2,000 and 5,000 Da. For example, glycol polymers, such as derivatives of polyethylene glycol (PEG), polyoxyethylenes, polymethylene glycols, polytri-methylene glycols and polyvinylpyrrolidones (PVP), and with povidone, per the Merck Index, 9th ed., p. 996, No. 7498. Derivatives of PEG, fungicides and bactericides such as Proxcel CRL, lysozyme, and foam stabilizers, may also be used. Surfactants, such an nonionic surfactants, cationic surfactants, anionic surfactants, and amphoteric surfactants, fatty acids, helianthinin and sunflower albumins (SFAs), egg white (albumen), fluorocarbon and hydrocarbon surfactants, may also be added, as may coloring agents, modifiers, and preservatives, natural cellulosic fiber, plasticizer, blowing agent, nucleating agent, metallic salt hydrate, and cross-linking reagents, and other property modifiers.

Synthetic coloring agents for contrast on the wound dressing may include azo dyes such as Amaranth, Ponceau 4R, Tartrazine, Sunset Yellow, Indigo Carmine. Natural coloring agents include xanthophyll, chlorophyll, and metallic oxides. As discussed above, biologically active substances may also be used to enhance binding or viscosity. These may include vascular endothelial growth factor [VEGF], endothelial cell growth factor (ECGF), basic fibroblast growth factor [bFGF], and bone morphogenic protein [BMP].

Starch, dextran or hyaluronic acid are also useful ingredients. Such starches can include corn starch, including maize, waxy maize, and high amylose corn starch, potato starch, sweet potato starch, wheat starch, rice starch, tapioca starch, sorghum starch, and a combination, hydroxyethyl starch, hydroxypropyl starch, carboxymethyl starch, acetylated high amylose starch, starch acetate, starch maleate, starch octenylsuccinate, starch succinate, starch phthalate, hydroxy-propylate high amylose starch, cross-linked starch, starch phosphates, hydroxypropyl distarch phosphate, cationic starch, starch propionamide, and combinations thereof.

Other additives may include radioprotective agents, vitamins, hormones, steroid derivatives, antibiotics, vaccines, antiviral agents, antifungal agents, antiparasitic agents, antioxidants, antitumor agents, anticancer agents, toxins, enzymes, enzyme inhibitors, proteins, peptides, inorganic compounds (e.g., zinc, copper, selenium, calcium derivatives), neurotransmitters, lipoproteins, glycoproteins, immunomodulators, immunoglobulins and fragments thereof, contrast agents, fatty acid derivatives, nucleic acids (e.g., DNA, RNA fragments) and polynucleotides, biological tissues, including live tissues and cells from these tissues, milk, clupeine, lysozyme, thaumatin and monellin. In addition, micro-sized particles and nanoparticles or suspensions may be used for their antimicrobial or antibacterial properties, such as silver or titanium oxide particles, or other oligodymanic metals or compounds. Sulfonamide nanocrystals, or nanoparticles of other antibiotics, antimicrobials or other medicaments, may also be used.

Contrast agents may also be used, such as diatrizoate (meglumine), iodecol, iodixanol, iofratol, iogulamide, iohexyl, iomeprol, iopamidol, iopromide, iotrol, ioversol, ioxaglate and metrizamide and mixtures thereof. Also useful are calcium compounds, and other substances from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate, polylactide, polyglycolide, polycaprolactone, polytrimethylene carbonate, and any combination thereof.

The gas used in embodiments can include air or one or more of the components of air, for example, nitrogen, oxygen, or carbon dioxide. Aqueous protein solutions (i.e., solutions containing globular proteins) are also used to form emulsions with oil phases. Such emulsions are used in manufactured foodstuffs such as mayonnaises and sauces. It is generally desirable that such emulsions should be stable during storage for long periods.

Thrombin Inhibitors

As noted above, once the foamed fibrinogen and the foamed thrombin are mixed, with a highly enlarged surface area, they react rapidly to form a fibrin foam in a very convenient and efficient manner. In some applications, it is desirable to inhibit this reaction, such as to allow the surgeon additional time for the procedure at hand or insure that the foamed fibrin is properly placed. Accordingly, inhibitors may be added to the thrombin portion of the components discussed above in order to delay the curing of the fibrin foam. One particularly useful type of inhibitor is an inhibitor that is photosensitive, i.e., the photosensitive compound delays curing until the compound is activated with light. Activation takes place when the fibrin foam is subjected to strong light or by irradiation with light of a certain wavelength. Of course, the photo-sensitive inhibitor must not be harmful to the patient, to the thrombin, or to the fibrin foam.

Such photo-sensitive inhibitors are disclosed in U.S. Pat. No. 5,318,524, the entire contents of which are hereby incorporated by reference, as though each word and disclosure were set forth herein, page for page and word for word. Examples of such photoinhibitors include, but are not limited to: 4-amidino-phenyl-2-hydroxy-4-diethylamino-alpha-methylcinnamate hydrochloride; a cinnamoyl derivative; and D-phenylalanyl-L-prolyl-L-arginine chloromethyl ketone. In previous experiments, an amount of inhibitor was added to the thrombin, which may then kept in the dark for long periods of time, even when mixed with fibrinogen. Upon exposure to light, the mixture reacts and forms fibrin. An amount effective to inhibit the reaction is used, and is then overcome by exposure to light. An alternative to speed up the reaction is to irradiate the foamed fibrin with light of a suitable wavelength, such as by irradiating fibrin foam, to which an effective amount of D-phenylalanyl-L-prolyl-L-argininechloromethylketone has been added, with a 350 nm wavelength light.

Thrombin Substitutes

While thrombin is clearly the predominant component used to react fibrinogen to form fibrin, other chemical species, known here as thrombin substitutes or clotting proteins, may also be used. For example, trisodium citrate has been added to a prothrombin complex (PTC) from human plasma to produce a thrombin substitute or clotting protein. See E. Shanbrom et al., *J. Thrombosis and Haemostasis,* 1 Suppl. 1 Jul. 2003. In addition, other thrombin substitutes are disclosed in U.S. Pat. Appl. Publ. 2003/0146113, including p-aminoaniline derivates, such as $R_1R_2$—N-phenyl-NH—CO-Arg-Pro-Gly-Tosyl, in which $R_1$ may be alkyl or hydrogen and in which $R_2$ may be hydrogen or hydroxyalkyl. The phenyl group may also be a single-substituted phenyl, the substitution including halogen, alkoxy, or alkylthio. This molecule has at least a minimal protein structure, that is, a linear chain joined together by peptide bonds between the carboxyl and amino groups of adjacent amino acid residues. Other clotting proteins include such thrombin-like enzymes as salmonase precursor, snake venom thrombin-like enzymes (SVTLEs), gabonase, ancrod, batroxobin, bilineobin, bothrombin, calobin, catroxobin, cerastobin, crotalase, flavoxobin, gabonase, grambin, habutobin, okinaxobin I, okinaxobin II, stenoxobin, thromboxytin and prothrombin. In terms of their use in wound dressings, these clotting proteins, and others with similar structures, are clearly equivalent to thrombin, at least in their clotting effect. Fibrinogen can be from plasma (3 mg/ml), recombinant from autologous preparation (up to 35 mg/ml), plasma enriched in fibrinogen (10 mg/ml), or concentrate as for our fibrin sealant (up to 100 mg/ml). Of course, lower concentrations may used and clotting time compensated for by increasing the thrombin concentration.

Fibrinogen and thrombin are also available commercially as fibrin glues such as BERIPLAST® from Aventis Behring, BIOCOL® from LFB, BOHELAL® from Kaketsuken, QUIXIL™ from Omrix, and HEMASEEL® from Hemacure. In addition, home made glues are known from automated systems such as VIVOSTAT™v, CRYOSEAL®, AUTOSEAL™ and BIOCORAL®, as well as plasma derivative sealants such as FIBRX™ from Cryolife Platelet Development Growth Factor (PDGF) and Bone Morphogenic Proteins (BMP)

It is also possible to add other agents, such as healing agents, antibiotics, drugs or hormones to one or more of the components. For example, additives such as Platelet Derived Growth Factor (PDGF), Bone Morphogenic Proteins (BMP), as modied bioactive fusion proteins, or Parathyroid Hormone (PTH), such as those manufactured for Kuros Biosurgery AG of Zurich, Switzerland, may be added to one of the fibrin-forming components, such as fibrinogen The self-assembly step mentioned above is enhanced if the mixture includes a growth factor, such as PDGF, especially PDGF that includes an additional amino acid sequence at one or both ends of the protein or peptide that constitutes the growth factor. The additional amino acid sequence is a transglutaminase substrate domain, i.e., a domain that crosslinks into the fibrin network during its formation in the presence of Factor XIII, thrombin, and a calcium source. The additional amino acid sequence is designed to contain an enzymatic cleavage site. This technology, known as TG-PDGF, enables the retention of a growth factor within a fibrin matrix during the process of wound healing. This technology was developed by Kuros Biosurgery AG of Zurich, Switzerland. As used herein, the term PDGF includes TG-PDGF.

As part of the healing process, cells grow through the matrix and remodel it. During the remodeling phase, the cells release enzymes which cleave the enzymatic degradation site in the additional amino acid sequence, thereby releasing the unmodified version of the growth factor or peptide. Subsequently, the released growth factors and peptides trigger the body's own healing mechanisms. Using this technology, even low doses of growth factors, peptides, or other bioactive factors show efficacy since diffusion or burst release is avoided. The fibrin matrix allows incorporation of other materials, such as cells or materials that increase mechanical stability of the fibrin, including calcium sources such as hydroxylapatite or calcium phosphate.

Testing was conducted while preparing formulations for wound dressing using varied concentrations of thrombin, as well as fibrinogen concentrations greater than 50 mg/ml. The testing included concentrations of fibrin stabilizing Factor XIII, also known as FXIII. The testing used FXIII concentrations greater than 0.5 IU/ml, and different concentrations of PDGF, such as 33, 100, and 300 μg/ml. Other concentrations, at least up to 1000 μg PDGF per ml may also be used.

Bone morphogenic proteins (BMP) may also be employed. By way of example, other agents include celluloses, such as hydroxypropylmethylcellulose, carboxylmethylcellulose and other celluloses, chitosan, photo-sensitive inhibitors of thrombin and thrombin-like molecules, self assembling amphiphile peptides designed to mimic aggregated collagen fibers (extracellular matrices), Factor XIII, cross-linking agents, pigments, fibers, polymers, copolymers, antibody, antimicrobial agent, agents for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, growth factors for heparin bonding, and anti-cholesterol drugs. Collagen, osteoblasts, and the like, and mixtures thereof, may also be used.

For example, statins may be used, such as atorvastatin (Lipitor®), simvastatin (Zocor®, Lipex®, Simvar®), Pravastatin (Pravachol®), Fluvastatin (Vastin®, Lescol®). Local anesthetics may also be used, such as esters and amides. Esters include, but are not limited to, cocaine, procaine (Novocain®), benzocaine (Cetacaine®), tetracaine and chloroprocaine (Nescaine®). Amides include, but are not limited to, lidocaine, xylocaine, mepivacaine (Polocaine®, Carbocaine®), bupivacaine (Marcaine®), and etidocaine (Duranest® and Prilocaine®).

Further examples of such agents also include, but are not limited to, antimicrobial compositions, including antibiotics, such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, fluconazole and glucanase, such as fluconazole 1 mg/ml in combination with glucanase 2.5 U/ml, and the like; and antiparasitic agents, such as pentamidine, and the like. Other agents may further include anti-inflammatory agents, such as alpha- or beta- or gamma-interferon, alpha- or beta-tumor necrosis factor, and the like, and interleukins.

It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of forming a fibrin foam, the method comprising:
preparing a fibrinogen foam by mixing air with a solution of fibrinogen using a mixer comprising a sintered polymeric material forming a three-dimensional lattice defining a plurality of tortuous interconnecting passages therethrough, the mixer having physical characteristics to sufficiently mix the components; and
injecting the fibrinogen foam into a solution of thrombin to form a fibrin foam.

2. The method of claim 1, further comprising applying the fibrin foam to a wound surface, and optionally, wherein the fibrin foam has a viscosity sufficient for a thin coating of the fibrin foam to adhere to a vertical surface.

3. The method of claim 1, wherein a rate of formation of the fibrin foam is constant in a temperature range from about 15° C. to about 37° C.

4. The method of claim 1, wherein the fibrinogen foam is prepared by mixing in a mixing device with at least two chambers having an inline mixer therebetween.

5. The method of claim 1, further comprising inhibiting the forming of the fibrin foam by adding an effective amount of a photosensitive inhibitor to the solution of thrombin.

6. The method of claim 1, further comprising lyophilizing the foam to form a lyophilisate, and optionally grinding the foam or the lyophilisate into a powder.

7. The method of claim 6, further comprising reconstituting the fibrin foam by mixing with water or a water solution and optionally adding an additional component.

8. The method of claim 1, further comprising selecting a container for holding the solution of thrombin and receiving the fibrinogen foam, wherein the fibrin foam takes a shape of the container.

9. A method of forming a fibrin foam, the method comprising:
preparing a fibrinogen foam by mixing air with a solution of fibrinogen using a mixer comprising a sintered polymeric material forming a three-dimensional lattice defining a plurality of tortuous, interconnecting passages therethrough, the mixer having physical characteristics to sufficiently mix the components in a hand-held mixing device; and
injecting the fibrinogen foam into a solution of thrombin to form a fibrin foam.

10. The method of claim 9, wherein the fibrin foam comprises at least fifty percent voids by volume, and optionally, wherein the fibrin foam is an open cell foam.

11. The method of claim 9, wherein the solution of fibrinogen or the solution of thrombin includes an effective amount of an additive wherein particles of the additive are sized between one micrometer and one nanometer in a major dimension of the particles.

12. The method of claim 9, wherein the fibrinogen is made from a solution having a concentration from about 1 mg/ml to about 110 mg/ml fibrinogen and wherein the thrombin is made from a solution of thrombin having a concentration from about 0.01 IU/ml to about 500 IU/ml.

13. The method of claim 9, further comprising a therapeutic amount of an agent, a drug, an antibiotic, a free growth factor, or a bioactive fusion protein in the solution of fibrinogen or in the solution of thrombin.

14. The method of claim 9, wherein the fibrinogen further comprises from about 10 to about 1000 μg PDGF, PTH or BMP per ml.

15. The method of claim 9, wherein the fibrinogen further comprises from about 10 to about 1000 μg free growth factor or bioactive fusion protein.

16. A method for forming a fibrin foam, the method comprising:
preparing a fibrinogen foam by mixing a fibrinogen solution and air using a mixer comprising a sintered polymeric material forming a three-dimensional lattice defining a plurality of tortuous, interconnecting passages therethrough, the mixer having physical characteristics to sufficiently mix the components; and
injecting the foam into a solution of a clotting protein to form a fibrin foam.

17. The method of claim 16, wherein the clotting protein is selected from the group consisting of thrombin, a PTC-derived thrombin substitute, and a p-aminoaniline-based protein.

18. The method of claim 16, further comprising applying the fibrin foam to a wound of a patient.

19. The method of claim 16, further comprising selecting a container for holding the solution of the clotting protein, wherein the fibrin foam takes the shape of the container upon forming.

20. The method of claim 16, further comprising mixing at least one of the solutions with a therapeutic amount of a calcium-containing compound, an agent, a drug, an antibiotic, or a hormone.

21. The method of claim 16, wherein at least the step of preparing takes place in a hand-held mixing device.

22. The method of claim 16, wherein at least the step of preparing takes place in a hand-held mixing device having at least two chambers with an inline mixer therebetween.

23. The method of claim 16, wherein the fibrinogen solution or the solution of the clotting protein further comprises an additive.

24. A method of forming a fibrin foam, the method comprising:
preparing a fibrinogen foam by mixing air with a solution of fibrinogen using a mixer comprising a sintered material forming a three-dimensional lattice defining a plurality of tortuous interconnecting passages therethrough, the mixer having physical characteristics to sufficiently mix the components, the sintered material comprising one of glass, ceramic and metal; and
injecting the fibrinogen foam into a solution of thrombin to form a fibrin foam.

25. The method of claim 24, further comprising applying the fibrin foam to a wound surface, and optionally, wherein the fibrin foam has a viscosity sufficient for a thin coating of the fibrin foam to adhere to a vertical surface.

26. The method of claim 24, wherein a rate of formation of the fibrin foam is constant in a temperature range from about 15° C. to about 37° C.

27. The method of claim 24, wherein the fibrinogen foam is prepared by mixing in a mixing device with at least two chambers having the inline mixer therebetween.

28. The method of claim 24, further comprising inhibiting the forming of the fibrin foam by adding an effective amount of a photosensitive inhibitor to the solution of thrombin.

29. The method of claim 24, further comprising lyophilizing the foam to form a lyophilisate, and optionally grinding the foam or the lyophilisate into a powder.

30. The method of claim 29, further comprising reconstituting the fibrin foam by mixing with water or a water solution and optionally adding an additional component.

31. The method of claim 24, further comprising selecting a container for holding the solution of thrombin and receiving the fibrinogen foam, wherein the fibrin foam takes a shape of the container.

* * * * *